United States Patent [19]

Nosari

[11] 3,998,210
[45] Dec. 21, 1976

[54] METHOD OF LOCATING VEIN
[75] Inventor: Elmo R. Nosari, Del Mar, Calif.
[73] Assignee: Gate Industries, Inc., San Diego, Calif.
[22] Filed: July 30, 1974
[21] Appl. No.: 493,347
[52] U.S. Cl. .......................... 128/2 H; 23/230 LC; 73/356; 128/DIG. 5
[51] Int. Cl.$^2$ ..................................... A61B 10/00
[58] Field of Search ............. 128/2 R, 2 H, DIG. 5; 73/356; 23/230 LC

[56] References Cited
UNITED STATES PATENTS

| | | | |
|---|---|---|---|
| 3,533,399 | 10/1970 | Goldberg et al. | 128/2 H |
| 3,594,126 | 7/1971 | Fergason et al. | 23/230 LC |
| 3,620,889 | 11/1971 | Baltzer | 23/230 LC X |
| 3,661,142 | 5/1972 | Flam | 128/2 H |
| 3,830,224 | 8/1974 | Vanzetti et al. | 128/2 H |

OTHER PUBLICATIONS

Tech. Concentrates – "Liquid Crystal Tape," Chem. & Engr. News, Oct. 25, 1971.

Primary Examiner—Dalton L. Truluck
Attorney, Agent, or Firm—Ellsworth R. Roston

[57] ABSTRACT

A laminate includes a backing of generally flexible, transparent sheet material supporting a particular layer of encapsulated liquid crystal material having properties for providing color variations in response to slight variations in temperature. A mixture of adhesive and ink is provided and disposed on the particular layer in a preferred method of making the laminate. The laminate is particularly useful in locating veins prior to the taking of a blood sample or prior to an invasive process of inserting fluids into a patient. The laminate can be adhered to the skin and the non-visible temperature pattern of the skin, including the generally hotter areas associated with the veins, will provide the liquid crystal material with a corresponding visual color pattern. The pattern will include a stripe of color indicating the location of the vein to facilitate the taking of the blood sample from the vein or the insertion of fluid into the vein by an invasive process. The invention relates to the article, method of forming the article and method of determining the position of veins on a human being.

9 Claims, 3 Drawing Figures

METHOD OF LOCATING VEIN

BACKGROUND OF THE INVENTION

1. Field of the Invention

This invention relates generally to temperature sensitive films and more specifically to the use of such a film to aid in locating the veins in the arm, hand or any prefixed area of a patient prior to taking a blood sample or the infusion of fluid into the patient by invasive techniques. The invention relates generally to the temperature sensitive film and specifically to the method of using the film.

2. Description of the Prior Art

One of the most common medical tests or procedures performed on patients is associated with the analysis of the blood of the patient or the infusion of fluid into the patient by invasive techniques. Usually the first step in such a test procedure involves the taking of a sample of the patient's blood or the infusion of fluid into the patient by invasive techniques. Typically by puncturing a vein in the arm of the patient using a needle and syringe or a needle set. Of course, in order to puncture the vein of the patient, the vein must first be located in the arm.

The location of the vein is not particularly difficult if it can be visually sighted or felt. In order to enhance the probability of visual sighting or feeling, an elastic strap is usually tightly wound around the upper arm of the patient. This produces a differential in the pressure of the blood being conducted by the veins. The human body responds to such a pressure differential by enlarging the veins in an attempt to provide a conduction path of less resistance. The enlarging of the veins makes them more prominent and therefore increases the probability that one of the veins can be located by viewing or feeling the arm of the patient.

Even when this procedure for enlarging the veins has been followed, there have been many cases where the veins could neither be sighted nor felt. Many factors are responsible for this result. Since the vein is generally dark in color, it is even more difficult to sight a vein in the arm of a person having a dark colored pigment in his skin. Other characteristics of the patient which make it particularly difficult to sight or feel a vein are associated with small children, obesity, and old age. These characteristics generally mean that the vein is significantly recessed from the skin and therefore particularly difficult to visually sight or feel.

In those cases where the vein can neither be sighted nor felt, a blood sample is typically taken only after repeatedly puncturing the arm of the patient or probing within the arm of the patient in an attempt to locate the vein. This of course is painful to the patient during the probing process and often leaves the patient with a substantial bruise after the blood sample is taken.

Liquid crystal materials are generally well known to provide a colorplay temperature range within which the material will provide color variations in response to different temperatures of the material in the colorplay range. The liquid crystal material has been enclosed in capsules which in turn have been drawn down on a plastic backing in a vacuum chamber to provide a particular layer of the encapsulated liquid crystal material. A black ink has been used to cover the particular layer to facilitate the detection of the color differences of the liquid crystal material. Such a device appears to have been disclosed in an Information and Instructions notice Number 711317-1 (Rev. 11-69) prepared by Edmund Scientific Co., Barrington, New Jersey. The process of drawing the encapsulated liquid crystal material onto the backing in a vaccum chamber has provided significant variations in the thickness of the particular layer. For example, the thickness has varied as much as 50 percent of the maximum thickness of the layer over approximately 90 percent of the layer. These variations in the thickness of the layer have left the layer with voids and also reduced the sensitivity of the temperature sensitive film to slight variations in temperature. Furthermore, the thickness of the different layers have been so thick that a low sensitivity of the resultant article has resulted when the articles have been placed upon a patient's skin. This has prevented such articles from indicating the location of veins on a patient.

SUMMARY OF THE INVENTION

The temperature sensitive film of the present invention includes an encapsulated material which may be a liquid crystal material having a colorplay range including the temperature of approximately 30° C. to 33° C., the average skin temperatures of a human being. In taking a blood sample, a strip of the film can be placed on the skin of the patient in transverse relationship to the veins in the arm of the patient. The relatively hot veins of the patient will provide the skin in closest proximity to the veins with a higher temperature than the remaining areas of the skin. The resulting temperature pattern of the skin provides the contiguous temperature sensitive film with a corresponding color pattern. By merely viewing the color pattern of the temperature sensitive film, particularly along the edge of the strip, one can locate the generally hotter area of the skin associated with the vein. This greatly facilitates the taking of blood samples, particularly from veins which can neither be visually sighted nor felt.

One embodiment of the temperature sensitive film has a MYLAR (polytetrafluoroethylene) backing which can be provided with a thickness no greater than 4 mils, and preferably less than 4 mils, to increase the flexibility of the film. The encapsulated liquid crystal material may be coated on this backing as by roll coating to provide the particular layer with a thickness which varies only approximately 40 percent of the maximum thickness of the layer over approximately 90 percent of the layer. Thus, the thickness variations of the particular layer are reduced by approximately 20–30 percent over the devices of the prior art. The coverage of the particular layer provided by the roll coating process is increased from approximately 94 percent with the present film. By roll coating the encapsulated film, the thickness of the film is maintained at a minimum value. This reduction in thickness variations and increase in coverage provides the temperature sensitive film of the present invention with a high degree of sensitivity so that the color pattern produced by the liquid crystal material is particularly accurate in providing an indication of temperature patterns. Furthermore, the sensitivity of the temperature sensitive film is considerably enhanced by providing the Mylar backing 14 and the encapsulated film with minimum thickness.

A suitable material such as a black ink may be mixed with an adhesive to provide a background layer ink in contiguous relationship with the particular layer. The dark background layer enhances the visual characteristics of the color pattern in the particular layer.

In the normal procedure for taking a blood sample, the area of the skin upon which the temperature sensitive film is to be placed is typically swabbed with alcohol or other cleansing agent, such as acetone, iodiozone, or extadene. When the temperature sensitive film is placed in contact with the swabbed area, the alcohol and the cooling of the flesh cause the adhesive in the background layer to harden. The alcohol also tends to dissolve the capsules of the liquid crystal material in the particular layer. Both of these features enhance the desirability of disposing of the temperature sensitive film once it has been used. It is desirable in the interest of sterility, to encourage the disposability of many medical devices.

The features and advantages associated with the apparatus and method of the present invention will become more apparent with a description of preferred embodiments of the temperature sensitive film and preferred method steps associated with use of the film. These preferred embodiments and methods will be discussed with reference to the associated drawings.

DESCRIPTION OF PREFERRED EMBODIMENTS

Figure 1:
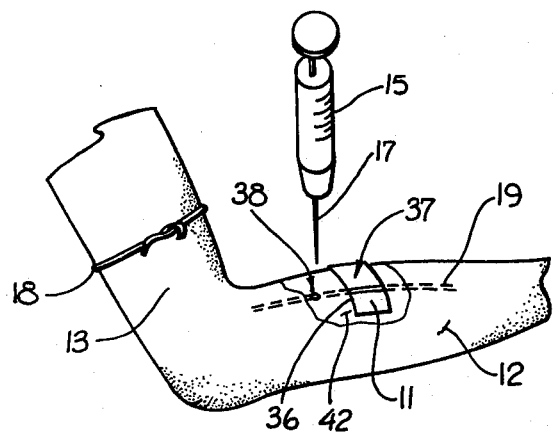
FIG. 1 illustrates the arm of a patient and a preferred method for taking a blood sample from the arm using the temperature sensitive film of the present invention or for infusing fluid into the blood by invasive techniques.

A preferred method for taking a blood sample or infusing fluid into a patient's blood by invasive techniques is illustrated in FIG. 1, wherein a strip of temperature sensitive film, shown generally at 11, is operably disposed in contact with the skin 12 on an arm 13 of a patient. A syringe 15 and associated needle 17 can be used in the normal manner to puncture a vein 19 in the arm 13 and withdraw a sample of the blood in the vein 19. Although there are many veins in the arm from which blood can be withdrawn, only the single vein 19 is illustrated in FIG. 1. In accordance with the usual procedure, an elastic strap 18 can be tightly wound around the upper portion of the arm 13 to enlarge the vein 19 and thereby facilitate the locating and puncturing of the vein 19.

Figure 2:
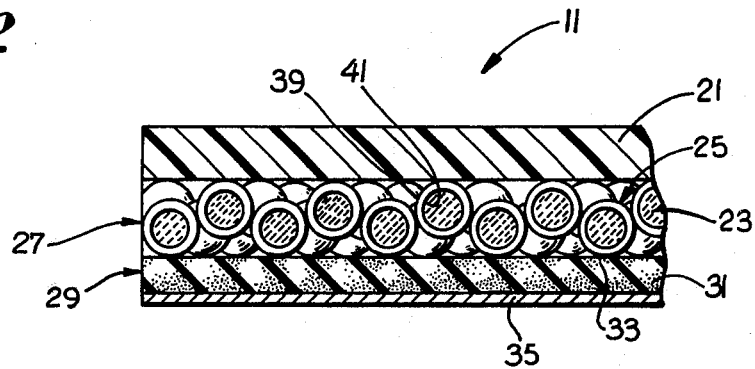
FIG. 2 is a cross-sectional view of the temperature sensitive film taken on the line 2—2 of FIG. 1.

In general, the temperature sensitive film 11 can be embodied as shown in FIG. 2. In this embodiment, a substantially transparent flexible backing 21 is provided. A suitable material such as liquid crystal material 23 is encapsulated to form a multiplicity of capsules or globules, shown generally at 25. The encapsulation may be provided as disclosed in U.S. Pat. No. 3,744,450 issued to Frank W. Godsey on Nov. 27, 1973, for a "Temperature Indicating Composition." The encapsulated liquid crystal material 23 is then coated on the backing 21 to form a first layer 27. A second layer 29 including a mixture of ink 31 and adhesive 33 is then disposed in contiguous relationship with the first layer 27. Instead of providing a single layer formed from a mixture of ink 31 and adhesive 33, separate thin layers of adhesive 33 and ink 31. A release paper 35 is disposed in contact with the second layer 29 to protect the adhesive 33 prior to use of the film 11.

This release paper 35 is typically removed before the second layer 29 of the film 11 is operably disposed in contact with the skin 12 of the patient.

As discussed in greater detail below, material such as the liquid crystal material 23 has properties for providing variations in color in response to slight temperature variations in a range of temperatures commonly referred to as the colorplay range. Suitable materials for use as the material 23 are disclosed in U.S. Pat. No. 3,700,603 issued to Allen Rembaum on Oct. 24, 1972, for "Heat Detection and Compositions and Devices Therefor" and in U.S. Pat. No. 3,620,889 issued to Donald H. Baltzer on Nov. 17, 1971, for "Liquid Crystal Systems." Materials capable of being used in the temperature range contemplated for this invention are also disclosed in U.S. Pat. No. 3,661,142 issued to Eric Flam on May 9, 1972, for "Temperature-Sensing Patch." When the temperature sensitive film 11 is operably disposed on the arm 13 of the patient, the liquid crystal material 23 in the first layer 27 provides a color pattern which can be viewed through the backing 21 and against the generally dark colored second layer 29 to indicate the location of the vein 19 in the arm 13.

It has been found that the temperature of the skin 12 in proximity to the vein 19 is generally greater than the temperature of the remaining portions of the skin 12. Thus, the skin 12 has a temperature pattern including areas of higher temperature in proximity to the vein 19. When the temperature sensitive film 11 is placed on the skin 12, the different surface temperatures of the skin 12, which characterize the temperature pattern, provide the liquid crystal material 23 in the first layer 27 with a color pattern corresponding to the temperature pattern. Included in this color pattern will be a colored stripe, shown generally at 37 in FIG. 1. This stripe 37 will appear on the temperature sensitive film 11 in closest proximity to the vein 19 in the arm 13. Thus, the stripe 37 in the color pattern of the temperature sensitive film provides an excellent indication of the location of the vein 19.

Having located the vein 19, the needle 17 associated with the syringe 15 can be inserted into the arm 13 at a point, such as the point 38, preferably in close proximity to the stripe 37 on the temperature sensitive film 11. Then the vein 19 can be punctured by the needle 17 and the syringe 15 operated to withdraw a sample of the blood. Alternatively, a needle may be inserted into the vein of the patient to infuse fluid into the vein by invasive techniques.

To facilitate the use of the temperature sensitive film 11 for locating veins, the backing 21 preferably has transparent characteristics so that the liquid crystal material 23 can be viewed through the backing 21. To facilitate the conformation of the film 11 to the arm 13 the backing 21 is preferably provided with a minimum thickness in keeping with a suitable strength. In the preferred embodiment, the backing 21 is formed from tetrafluoroethylene such as that manufactured by DuPont de Nemours Co. of Wilmington, Delaware, under the trademark "MYLAR". This material can be provided with a thickness of three mils to enhance the flexible characteristics of the film 11. Preferably this material may be provided with a thickness of less than 4 mils.

Materials such as liquid crystals are generally well known to reflect different colors in response to different temperatures in a colorplay range of temperatures. When the liquid crystals experience different temperatures in the colorplay range, they orient themselves in different directions to reflect incident light in different wave lengths corresponding to different colors in the spectrum. At the lower temperatures in the colorplay range, the liquid crystals have a generally red color. As their temperature increases within the colorplay range, however, the liquid crystals pass through the colors yellow and green to the color blue at the other end of the spectrum. In a preferred embodiment, the liquid crystal material 23 is provided with a colorplay range of approximately 29° C. to 35° C. It will be noted that this range includes the normal body temperature of human beings.

The color variations of the liquid crystal material 23 is response to temperature can occur an indefinite number of times. Thus the temperature sensitive film 11 can be used repeatedly to provide a visual indication of the temperature pattern of a contiguous surface. As discussed in greater detail below, it may be desirable to encourage disposability of the film 11 if it is to be used in a blood sampling procedure or it is to be used to infuse fluid into a patient by invasive techniques.

Although skin temperatures will differ for different patients, the stripe 37 in the color pattern will have a particular color such as blue or green, closer to the blue end of the spectrum, and the remaining colors in the color pattern will be the colors, such as yellow or red, closer to the red end of the spectrum. At temperatures below the colorplay range, the liquid crystal material is generally transparent so that the film 11, when viewed through the backing 21 and the first layer 27, will appear to have the color, such as black, of the ink 31 in second layer 29.

The temperature sensitive film 11 appears to be more sensitive to the temperature differentials along a longitudinal edge 36 of the film 11. This may be due to the fact that the heat present at the edge 36 is not shared with as great a mass of the film 11 as it is at the interior regions of the film 11.

It is particularly desirable to encapsulate the liquid crystal material 23 not only to inhibit its contamination but also to provide the liquid crystal material 23 with a dry coated form. The microcapsules microglobules 25 in the first layer 27 each have an outer wall 39 which defines a cavity 41. A portion of the liquid crystal material 23 is disposed in each of the cavities 41 to provide the encapsulated liquid crystal material in the first layer 27. The material forming the outer walls 39 of the globules 25 is preferably transparent so that the color variations of the liquid crystal material 23 in the cavities 41 can be viewed through the walls 39 and the backing 21. In preferred embodiments of the film 11 the walls 39 of the capsules 25 are formed from gelatin and saran. The microcapsules or microgobules 25 will typically have a generally spherical configuration with diameters in a range between 10 and 30 microns. Encapsulation techniques are disclosed in the following patents issued to National Cash Register Company: U.S. Pat. No. 2,374,862; 2,730,457; 2,730,456; 3,041,288; 3,041,289; 3,111,407; 2,940,847; 3,116,206; and 2,800,457.

To form the adhesive mixture in the second layer 29, the adhesive 33, such as rubber cement, can be combined with the ink 31 which preferably has a dark color, such as black. One of the purposes of this adhesive mixture is to maintain the first layer 27 of the encapsulated liquid crystal material 23 in close proximity to the skin 12 of the patient. The dark color of the adhesive layer 29 provides a dark background which absorbs any light passing through the liquid crystal material 23 and allows the selectively reflected light passing back through the backing 21 to be viewed without light interference. In other words, the adhesive mixture in the second layer 29 provides a dark background against which the color variations of the liquid crystal material 23 are particularly visible. It is particularly desirable that the ink 31 and the adhesive 33 are combined in a single layer 29 of the temperature sensitive film 11 to minimize the overall thickness of the vein finder constituting this invention. In this way, the vein finder is quite sensitive to variations in the temperature of the patient at adjacent positions on the skin of the patient. With respect to embodiments which might include the ink 31 and the adhesive 33 in separate layers, the single layer embodiment also provides a significant savings, not only in the number of procedural steps but also in the time consumed in making the film 11.

If the temperature sensitive film 11 is to be used in locating veins, such as the vein 19, it is particularly desirable that adhesive 33 include rubber cement. In the normal procedure for taking a blood sample or for infusing fluid into the blood of a patient by invasive techniques, the area of the skin 12 in proximity to the point of the incision is sterilized with alcohol. Such an area might be the area 42 illustrated in FIG. 1 enclosed by the line of the same numeral.

When operably disposed, the temperature sensitive film 11 will typically be placed over the sterilized area 42 with the second layer 29 in contact with the alcohol defining the area 42. With the film 11 thus positioned, the alcohol in the area 42 will tend to degrade the adhesive characteristics of the rubber cement in the layer 29; it may also tend to degrade the material forming the walls 39 of the capsules 25. The alcohol also tends to cool the area of the skin which it contacts.

Practically speaking, this degradation of materials will mean that the film 11 will not perform as effectively during a second use. Thus the formation of the second layer including rubber cement and the first layer including gelatin or saran will increase the desirability of disposing of the film 11 after a single use. This induced disposability is particularly appreciated when the film 11 is used with patients in a hospital procedure wherein sterility is of particular importance.

It is particularly desirable that the first layer 27 of the encapsulated liquid crystal material 23 have a substantially uniform thickness of minimum dimensions. If the thickness of the layer 27 varies significantly, the color variations in response to different surface temperatures will vary with the thickness. In the thicker regions of the layer 27, there will be a greater mass to dissipate the available heat. As a consequence, the thicker areas of the layer 27 will sense a cooler temperature and display a color closer to the red end of the spectrum. In the thinner regions of the area 27, there will be a lesser mass to dissipate the available heat. As a consequence, the thinner areas of the layer 27 will sense a hotter temperature and display a color closer to the blue end of the spectrum. Furthermore, if the layer 27 of the encapsulated material 23 is too thick, it will not provide a true indication of temperature at the outer surface of the layer. If the first layer 27 has a substantially uniform thickness of minimum dimensions however, the color of the liquid crystal material 23 will accurately reflect the relative temperature of the underlying surface, such as the area of the body on which the vein finder has been placed.

It is also desirable that the second layer 29, including the ink 31 and the adhesive 33, be of substantially uniform and minimum thickness. This is desirable since the heat from the underlying surface, such as the skin 12, must pass through the second layer 29 to effect a color variation in the liquid crystal material 23. In thinner regions of the second layer 29, a greater amount of heat will pass to the first layer 27 than in the thicker regions of the second layer 29. This, of course, will have a significant effect on color patterns provided by the liquid crystal material 23.

Figure 3:
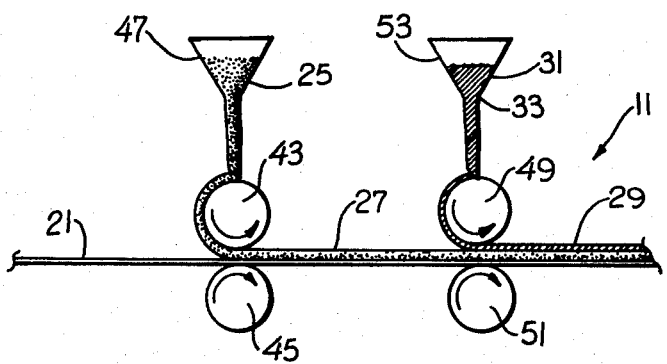
FIG. 3 illustrates a roll coating process for manufacturing the temperature sensitive film of the present invention.

In a preferred method of manufacturing the temperature sensitive film 11, the thicknesses of the first and second layers 27 and 29, respectively, can be maintained without significant variations and with minimum dimensions, in a roll coating process. As illustrated in FIG. 3, the backing 21 can be fed between a pair of rollers 43 and 45. A bin 47 is positioned above the rollers 43, 45 to deposit the encapsulated liquid crystal material 23 onto the roller 43. Then as the backing 21 passes between the rollers 43 and 45, the first layer 27 of the capsules or globules is roll coated onto the backing 21.

This combination of the backing 21 and the first layer 27 is fed between a second pair of rollers 49 and 51. A bin 53 is positioned above the rollers 49, 51 to deposit the mixture of ink 31 and adhesive 33 onto the roller 49. This results in the formation of the second layer 29 in contiguous relationship with the first layer 27.

In a preferred embodiment of the temperature sensitive film 11, the first layer 27 of the encapsulated liquid crystal material 23 has a thickness of approximately four mils. Using the roll coating process, illustrated in FIG. 3, this thickness can be maintained to within ± one mil over 90 percent of the area of the film 11. Thus, with reference to the prior art devices, the roll coating process provides a reduction in the thickness of the layer 27 and also a reduction in the variations in the thickness of the layer 27 and therefore significantly increases the accuracy of the color pattern produced by the liquid crystal material 23.

In a preferred embodiment of the film 11, the second layer 29 is provided with a thickness of approximately two mils. The roll coating process makes it possible to maintain the thickness of the layer 29 within ± one mil over approximately 90 percent of the area of the film 11. This provides the film 11 with a minimum thickness and minimum variations in thickness and thereby provides generally uniform heat transfer characteristics through the second layer 29. This even further increases the accuracy of the color pattern produced by the liquid crystal material 23.

Using the above described manufacturing process, the resulting film 11 is particularly desirable for locating the vein 19 prior to taking a blood sample from a patient or infusing fluid into a patient by invasive techniques. The minimum and substantially uniform thicknesses provided the first and second layers 27 and 29 of the film make the liquid crystal material 23 particularly accurate in providing a pattern having color characteristics dependent upon the heat characteristics of the portions of the body adjacent to the vein finder. This color pattern will include the strip 37 which may be most apparent along the longitudinal edge 36 of the film 11 By inserting the needle 17 into the arm 13 at a point 38 along an extension of the strip 37, the probability of puncturing the vein 19 can be considerably increased over the vein locating methods of the prior art. For example, accuracies in locating the vein have been increased by at least seventy five percent (75%) or more by using the vein finders of this invention.

Although the film 11 and the methods for manufacturing and using the film 11 have been specifically described, it will be apparent that the film 11 can be otherwise embodied and that the manufacturing process can include other steps all within the scope of the invention. Furthermore, the film 11 can be advantageously used to provide a visual indication of the temperature pattern of any underlying surface. For these reasons, the scope of the invention should be ascertained only with reference to the following claims.

I claim:

1. A method for taking a sample of blood from a vein of a patient or of infusing fluid into the vein of the patient by invasive techniques, the vein having a relatively high temperature providing the skin of the patient in proximity to the vein with a higher temperature than the remaining areas of the skin, the method including the steps of:

providing a thin temperature sensitive film of substantially uniform thickness of the order of a rew mils, the film including a multiplicity of microcapsules in a relatively high concentration with each microcapsule having a hollow interior enclosing within the hollow interior a liquid crystal material having properties instantaneously responsive to different temperatures of the liquid crystal material in a colorplay range of temperatures to vary the color of the liquid crystal material, and providing a thin backing of a substantially uniform thickness for the temperature sensitive film and providing on the temperature sensitive film a thin film of a substantially uniform thickness of a few mils of a combination of an adhesive and background means;

initially applying a solvent to the skin of the patient at a localized position overlying the vein of the patient to clean and cool the skin at this localized position;

immediately thereafter placing the temperature sensitive film in contiguous relationship with the skin of the patient at a localized position overlying the vein of the patient and with the adhesive film contacting the skin at the localized position, the crystal material in the temperature sensitive film being instantaneously responsive to the higher temperature of the body at positions in proximity to the vein to provide instantaneously and for a relatively short period of time a color pattern including a first color along the path of the vein and being responsive to the lower temperature of the remaining areas of the body contacted by the adhesive film to provide instantaneously and for the relatively short period of time in the color pattern a color other than the first color at the positions contiguous to such remaining area of the body;

inserting the needle of a syringe or set into the patient at a position along an extension of the path defined by the first color in the color pattern provided by the liquid crystal material so that the needle enters the vein; and operating the syringe to withdraw the sample of the blood from the vein or to infuse fluid into the vein of the patient by invasive techniques.

2. The method set forth in claim 1 wherein the temperature sensitive film is at least partially defined by a longitudinal edge and the placing step includes the step of positioning the temperature sensitive film in contiguous relationship with the skin of the patient with the longitudinal edge of the vein locating film in transverse relationship with the vein in the arm of the patient.

3. The method recited in claim 2 further comprising the steps of:
viewing the particular longitudinal edge of the temperature sensitive film to determine a particular point along the longitudinal edge at which the liquid crystal material has a color closer to the color blue in the spectrum than the other colors along the longitudinal edge; and
inserting the needle of the syringe or set into the arm of the patient in proximity to the particular point along the longitudinal edge of the temperature sensitive strip.

4. The method recited in claim 1 wherein during the providing step a layer of adhesive is disposed next to the capsules and a release paper is removably adhered to the adhesive layer to protect the adhesive layer, and the method further comprises, prior to the placing step, the step of removing the release paper from the adhesive layer to expose the adhesive layer and to facilitate the placing of the temperature sensitive film in contiguous relationship with the skin of the patient.

5. The method recited in claim 1 further comprising the steps of:
intimately mixing an adhesive and a dark colored background ink to form an adhesive mixture having dark opaque adhesive characteristics:
depositing the intimate mixture in contiguous relationship with the encapsulated liquid crystal material;
during the placing step, positioning the vein locating film on the arm of the patient with the adhesive mixture disposed in contiguous relationship with the skin of the patient; and
viewing the instantaneously produced color variations of the liquid crystal material against the dark, opaque background provided by the adhesive mixture.

6. A method of locating a vein of a patient for the purpose of taking a sample of blood from the patient or of infusing fluid into the vein of the patient by invasive techniques,
providing a thin temperature sensitive film having a substantially uniform thickness of a few mils and including a multiplicity of hollow microcapsules each having properties of passing light and each enclosing a chemical having properties of responding instantaneously to variations in temperature through a range of temperatures representative of temperatures on the skin of the patient to produce different colors in the chemical at such different positions in accordance with such variations in temperature at such different positions,
applying a solvent to a localized postion on the skin of the patient near the vein of the patient to sterilize and cool the skin at the localized position near the vein of the patient;
immediately thereafter disposing the thin temperature sensitive film on the skin of the patient at the localized position near the vein of the patient to obtain variations instantaneously and for only a relatively brief period of time in the color of the film at different positions in accordance with the variations in the temperature of the patient's body at such different positions; and
observing on the temperature sensitive film the positions which provide instantaneously and for only the relatively brief period of time the colors representative of the elevated temperature produced in the body of the patient by the proximity of the patient's vein.

7. A method as set forth in claim 6 wherein the temperature sensitive film is provided with a thin layer having a substantially uniform temperature response and having properties of adhering to the patient's skin in removable relationship to the skin and wherein the temperature sensitive film is disposed on the patient's skin with the adhering layer adhered to the skin.

8. The method as set forth in claim 7 wherein the solvent initially applied to the skin constitutes alcohol and wherein the adhering layer has properties of becoming degraded in alcohol to facilitate the removal of the temperature sensitive film from the patient's skin upon the initial application of alcohol to the skin and to inhibit the re-adherence of the adhering layer of the patient's skin.

9. A method as set forth in claim 7 wherein a release paper is normally disposed on the adhering layer and the release paper is removed from the adhering layer just prior to the adherence of the adhering layer on the patient's skin.

* * * * *